(12) United States Patent
Qiu

(10) Patent No.: US 9,700,693 B2
(45) Date of Patent: Jul. 11, 2017

(54) SYSTEMS AND METHODS FOR INTUBATION

(71) Applicant: Chunyuan Qiu, Huntington Beach, CA (US)

(72) Inventor: Chunyuan Qiu, Huntington Beach, CA (US)

(*) Notice: Subject to any disclaimer, the term of this patent is extended or adjusted under 35 U.S.C. 154(b) by 234 days.

(21) Appl. No.: 14/510,045

(22) Filed: Oct. 8, 2014

(65) Prior Publication Data

US 2015/0025368 A1    Jan. 22, 2015

Related U.S. Application Data

(60) Continuation of application No. 13/074,986, filed on Mar. 29, 2011, now Pat. No. 8,882,682, which is a (Continued)

(51) Int. Cl.
*A61B 5/00* (2006.01)
*A61M 16/04* (2006.01)
(Continued)

(52) U.S. Cl.
CPC ..... *A61M 16/0488* (2013.01); *A61B 1/00052* (2013.01); *A61B 1/05* (2013.01); *A61B 1/267* (2013.01); *A61B 5/0084* (2013.01); *A61B 5/03* (2013.01); *A61B 5/0538* (2013.01); *A61B 5/0836* (2013.01); *A61B 5/6852* (2013.01);
(Continued)

(58) Field of Classification Search
CPC .............. A61M 16/04; A61M 16/0411; A61M 16/0418; A61M 16/0488
See application file for complete search history.

(56) References Cited

U.S. PATENT DOCUMENTS 4,292,961 A    10/1981  Kawashima
4,366,810 A    1/1983   Slanetz, Jr.
(Continued)

FOREIGN PATENT DOCUMENTS

EP    0230790 A2    8/1987
WO    99/34726 A1   7/1999
(Continued)

OTHER PUBLICATIONS

ISA United Statement Patent and Trademark Office. International Search Report of PCT/US2008/073176, Nov. 14, 2008, 2 pages.
(Continued)

*Primary Examiner* — Max Hindenburg
(74) *Attorney, Agent, or Firm* — McCoy Russell LLP

(57) ABSTRACT

An intubation device is provided. An intubation device comprises a movable guide configured to guide an insertion of an endotracheal tube into a trachea of a patient, the guide having a guide extension and a guide tip; an external trachea identifier source external to the trachea and disposed on the patient during an intubation, wherein the trachea identifier source generates and transmits a signal; at least one trachea condition sensor disposed on the guide tip to detect the signal generated by the trachea identifier source; and a guide control device operatively coupled to the guide, the guide control device configured to move the guide into the trachea in response to the detected signal.

24 Claims, 5 Drawing Sheets

Related U.S. Application Data division of application No. 11/893,536, filed on Aug. 15, 2007, now Pat. No. 8,166,967.

(51) Int. Cl.

| | | |
|---|---|---|
| *A61B 5/03* | (2006.01) | |
| *A61B 1/00* | (2006.01) | |
| *A61B 1/05* | (2006.01) | |
| *A61B 1/267* | (2006.01) | |
| *A61B 10/04* | (2006.01) | |
| *A61B 18/20* | (2006.01) | |
| *A61M 25/01* | (2006.01) | |
| *A61B 34/20* | (2016.01) | |
| *A61B 34/30* | (2016.01) | |
| A61B 5/053 | (2006.01) | |
| A61B 5/08 | (2006.01) | |
| A61B 5/083 | (2006.01) | |
| A61B 5/087 | (2006.01) | |
| A61B 7/00 | (2006.01) | |
| A61M 16/00 | (2006.01) | |
| A61M 16/10 | (2006.01) | |
| *A61B 90/00* | (2016.01) | |

(52) U.S. Cl.
CPC ............ *A61B 10/04* (2013.01); *A61B 18/201* (2013.01); *A61B 34/20* (2016.02); *A61B 34/30* (2016.02); *A61B 90/39* (2016.02); *A61M 16/0003* (2014.02); *A61M 16/0051* (2013.01); *A61M 25/0116* (2013.01); *A61B 5/053* (2013.01); *A61B 5/087* (2013.01); *A61B 5/0813* (2013.01); *A61B 5/0833* (2013.01); *A61B 7/003* (2013.01); *A61B 2090/3975* (2016.02); *A61B 2090/3983* (2016.02); *A61M 2016/0027* (2013.01); *A61M 2016/0036* (2013.01); *A61M 2016/0413* (2013.01); *A61M 2016/1025* (2013.01); *A61M 2016/1035* (2013.01); *A61M 2202/0208* (2013.01); *A61M 2202/0266* (2013.01); *A61M 2202/0283* (2013.01); *A61M 2202/0291* (2013.01); *A61M 2205/3303* (2013.01); *A61M 2205/3306* (2013.01); *A61M 2205/3317* (2013.01); *A61M 2205/3375* (2013.01); *A61M 2205/3561* (2013.01); *A61M 2205/3584* (2013.01); *A61M 2205/502* (2013.01); *A61M 2210/1032* (2013.01); *A61M 2230/437* (2013.01)

(56) References Cited

U.S. PATENT DOCUMENTS

| | | |
|---|---|---|
| 4,469,091 A | 9/1984 | Slanetz, Jr. |
| 5,257,636 A | 11/1993 | White |
| 5,285,778 A | 2/1994 | MacKin |
| 5,445,161 A | 8/1995 | Huang |
| 5,492,131 A | 2/1996 | Galel |
| 5,560,351 A | 10/1996 | Gravenstein et al. |
| 5,591,130 A | 1/1997 | Denton |
| 5,951,461 A | 9/1999 | Nyo et al. |
| 6,063,093 A | 5/2000 | Winston et al. |
| 6,149,603 A | 11/2000 | Parker |
| 6,161,537 A | 12/2000 | Gravenstein et al. |
| 6,164,277 A | 12/2000 | Meridith |
| 6,203,493 B1 | 3/2001 | Ben-Haim |
| 6,289,238 B1 | 9/2001 | Besson et al. |
| 6,349,720 B1 | 2/2002 | Clark |
| 6,463,313 B1 | 10/2002 | Winston et al. |
| 6,468,203 B2 | 10/2002 | Belson |
| 6,659,962 B2 | 12/2003 | Ricciardelli |
| 6,705,320 B1 | 3/2004 | Anderson |
| 6,715,491 B2 | 4/2004 | Cooper et al. |
| 6,757,557 B1 | 6/2004 | Bladen et al. |
| 6,820,614 B2 | 11/2004 | Bonutti |
| 6,858,005 B2 | 2/2005 | Ohline et al. |
| 6,860,264 B2 | 3/2005 | Christopher |
| 6,869,396 B2 | 3/2005 | Belson |
| 6,890,297 B2 | 5/2005 | Belson |
| 6,926,709 B2 | 8/2005 | Bieger et al. |
| 6,970,732 B2 | 11/2005 | Winston et al. |
| 6,981,947 B2 | 1/2006 | Melker |
| 7,044,907 B2 | 5/2006 | Belson |
| 7,087,013 B2 | 8/2006 | Belson et al. |
| 7,089,928 B2 | 8/2006 | Besharim et al. |
| 7,174,202 B2 | 2/2007 | Bladen et al. |
| 7,178,519 B2 | 2/2007 | Melker et al. |
| 7,182,728 B2 | 2/2007 | Cubb et al. |
| 7,194,296 B2 | 3/2007 | Frantz et al. |
| 7,543,586 B2 | 6/2009 | Qureshi et al. |
| 8,166,967 B2 * | 5/2012 | Qiu ..................... A61B 5/0084 128/200.26 |
| 8,882,682 B2 * | 11/2014 | Qiu ..................... A61B 5/0084 128/200.26 |
| 2002/0074002 A1 | 6/2002 | Tung et al. |
| 2002/0173799 A1 | 11/2002 | Besharim et al. |
| 2003/0018276 A1 | 1/2003 | Mansy et al. |
| 2003/0034035 A1 | 2/2003 | Raphael |
| 2004/0039252 A1 | 2/2004 | Koch, III |
| 2004/0199053 A1 | 10/2004 | Boulais et al. |
| 2005/0076914 A1 | 4/2005 | Besharim et al. |
| 2005/0107669 A1 | 5/2005 | Couvillon, Jr. |
| 2005/0154261 A1 | 7/2005 | Ohline et al. |
| 2005/0187434 A1 | 8/2005 | Dey et al. |
| 2005/0209509 A1 | 9/2005 | Belson |
| 2006/0004258 A1 | 1/2006 | Sun et al. |
| 2006/0004260 A1 | 1/2006 | Boedecker et al. |
| 2006/0122460 A1 | 6/2006 | Kamali |
| 2006/0129055 A1 | 6/2006 | Orr et al. |
| 2006/0180155 A1 | 8/2006 | Glassenberg et al. |
| 2006/0201517 A1 | 9/2006 | Rich et al. |
| 2007/0015967 A1 | 1/2007 | Boulais et al. |
| 2007/0106117 A1 | 5/2007 | Yokota |
| 2007/0106121 A1 | 5/2007 | Yokota et al. |
| 2007/0106122 A1 | 5/2007 | Yokota et al. |
| 2007/0129603 A1 | 6/2007 | Hirsh |
| 2008/0216826 A1 | 9/2008 | Boyden et al. |
| 2009/0044799 A1 | 2/2009 | Qiu |

FOREIGN PATENT DOCUMENTS

| | | |
|---|---|---|
| WO | 2004/000107 A2 | 12/2003 |
| WO | 2009/023779 A1 | 2/2009 |

OTHER PUBLICATIONS

"Karl Storz Endoscopy-America, Inc." <http://www.anesthesiologynews.com/ancp/0808/content/ancp0808_042a.html?pagename=karl_storz_corporate_profile>, 2 pages. Accessed Dec. 4, 2009.

Wagner, Jason. "The Storz Video Laryngoscope." <http://www.epmonthly.com/subspecialties/technology/the-storz-video-laryngoscope/>, 3 pages. Accessed Dec. 4, 2009.

* cited by examiner

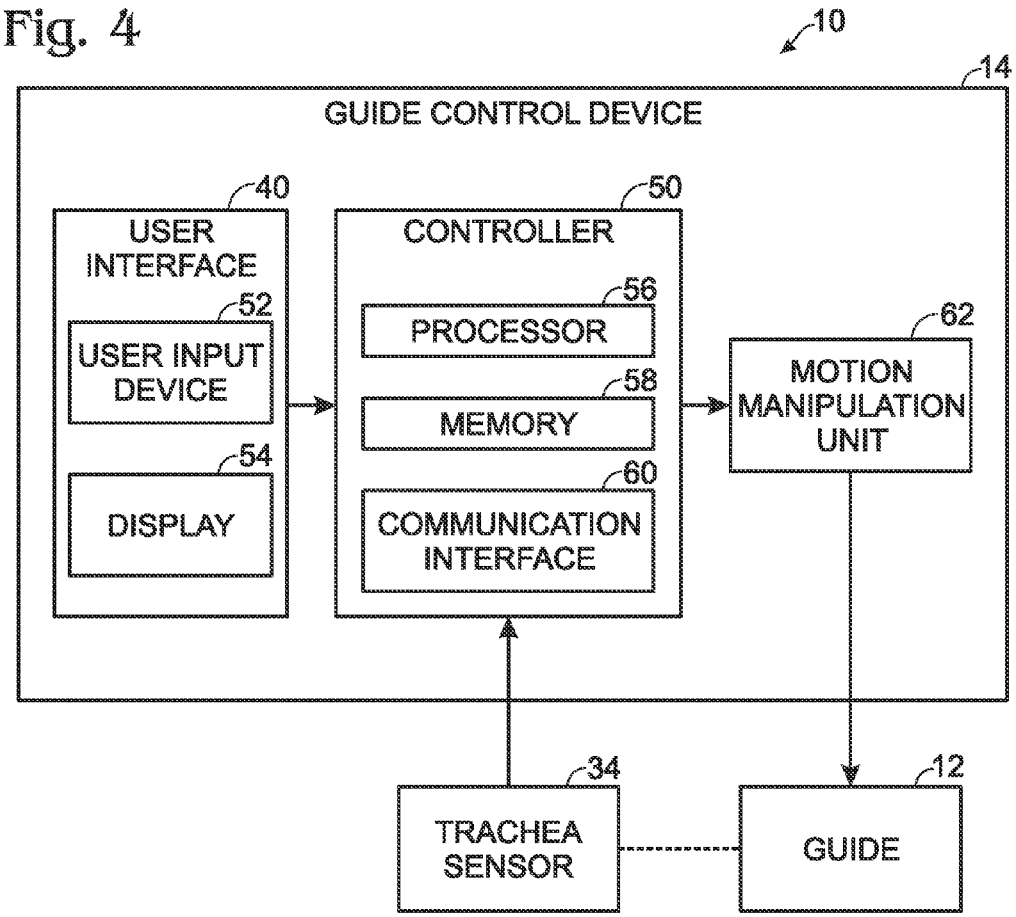
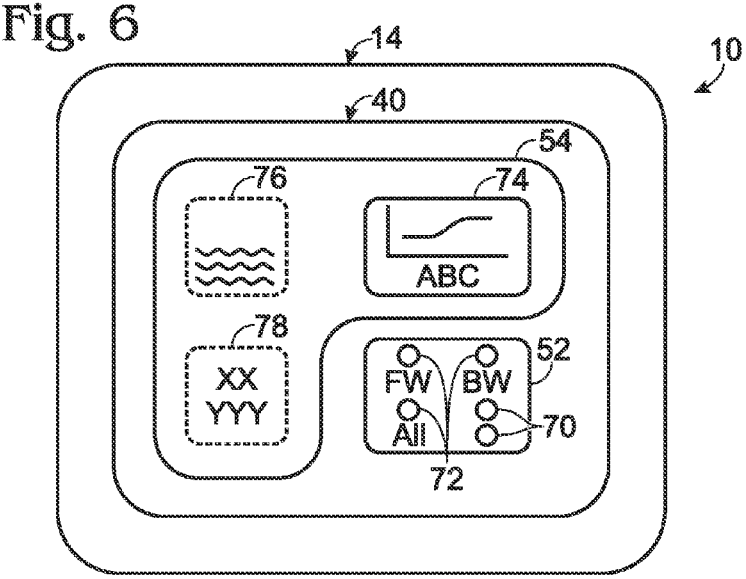

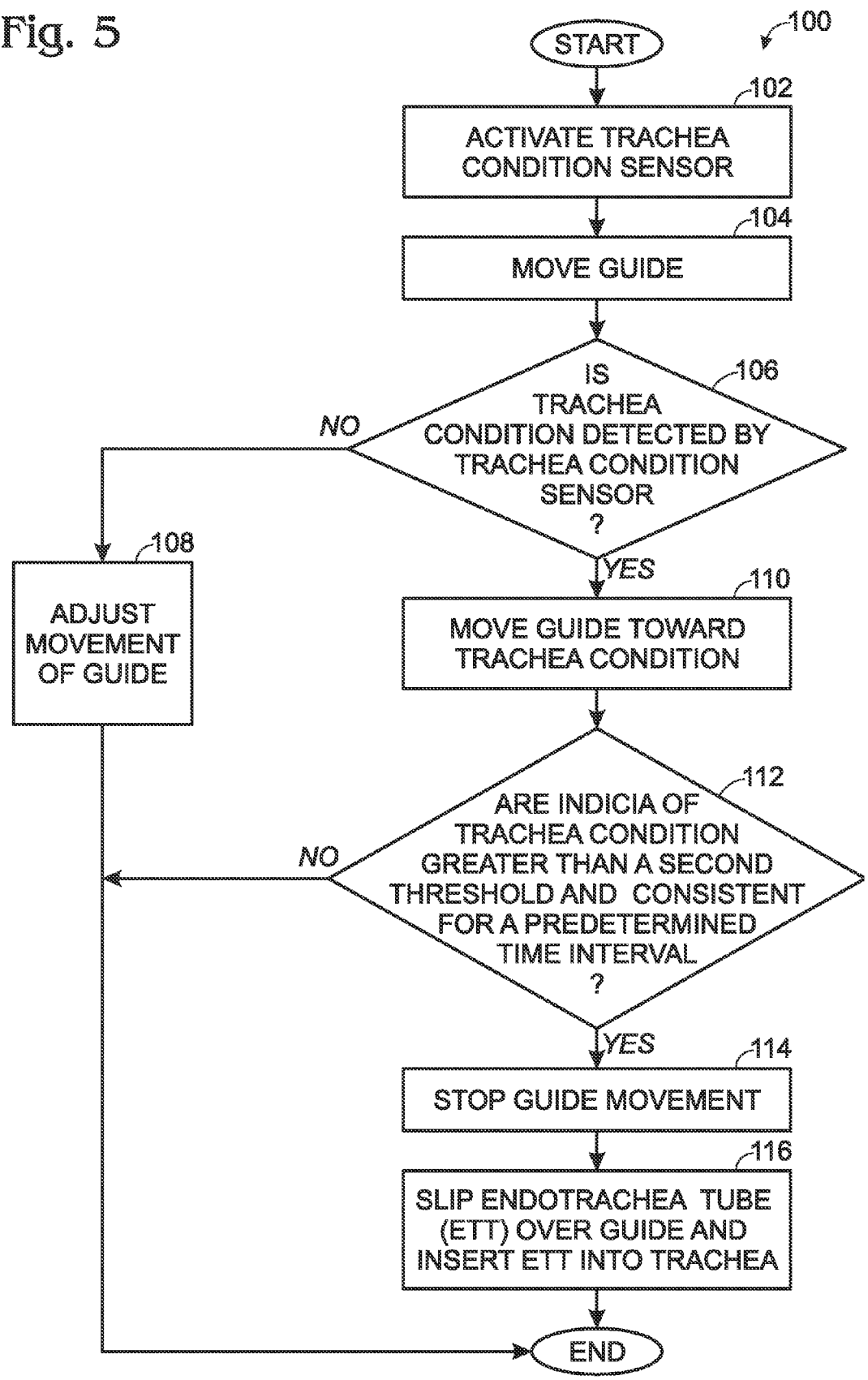

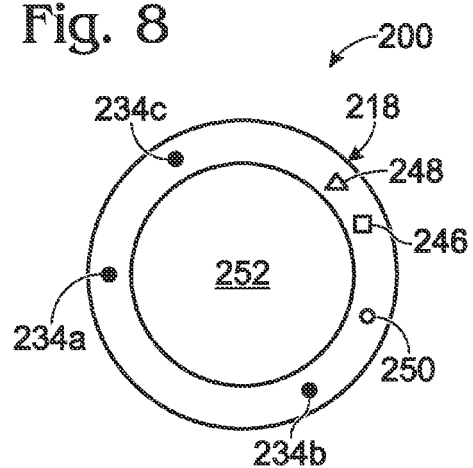
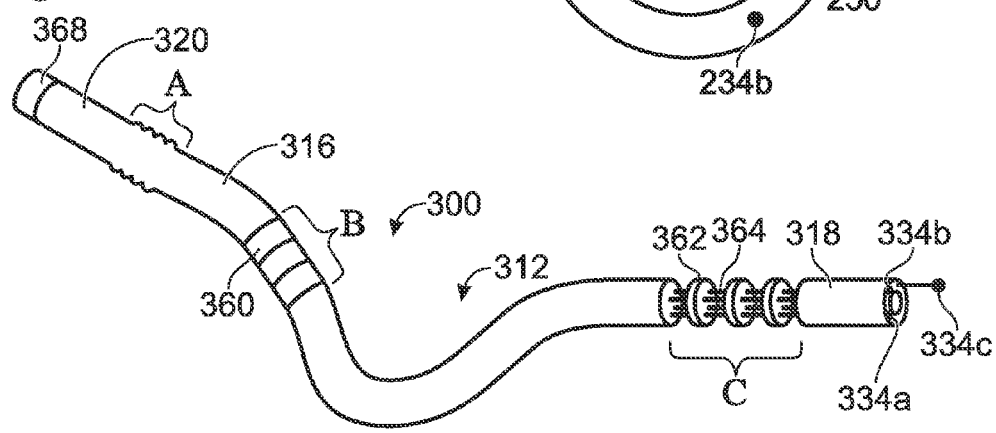
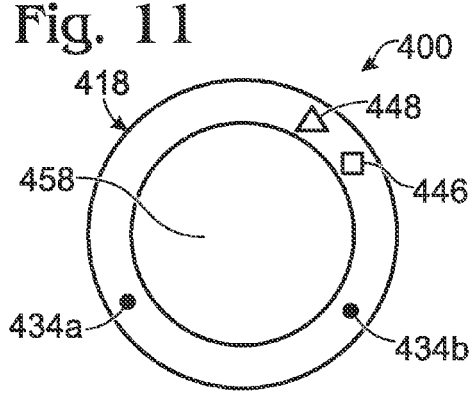
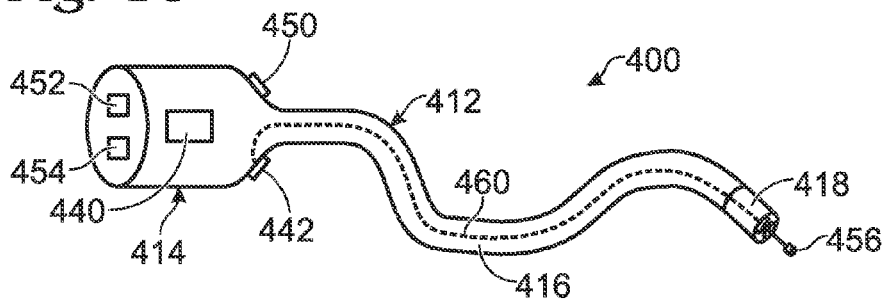

SYSTEMS AND METHODS FOR INTUBATION

CROSS REFERENCE TO RELATED APPLICATIONS

The present application is a continuation of U.S. patent application Ser. No. 13/074,986, "SYSTEMS AND METHODS FOR INTUBATION," filed Mar. 29, 2011, which is a divisional of U.S. patent application Ser. No. 11/893,536, "SYSTEMS AND METHODS FOR INTUBATION," filed on Aug. 15, 2007, now U.S. Pat. No. 8,166,967, the entire contents of each of which are hereby incorporated by reference for all purposes.

TECHNICAL FIELD

The present disclosure relates generally to systems and methods to intubate a patient, and more particularly to systems and methods to intubate a patient as guided by one or more trachea condition sensors.

BACKGROUND

Some medical procedures are invasive and potentially dangerous although they are necessary life-saving procedures. Intubation, specifically tracheal intubation, is typically performed at various medical conditions, such as application of general anesthesia, comatose, etc. Tracheal intubation involves the placement or the insertion of an endotracheal tube (ETT) into a patient's trachea to protect the patient's airway and provide a means of mechanical ventilation. Delay and/or misplacement of the endotracheal tube, such as misplacement of the endotracheal tube into esophagus, may cause permanent neurological damage or death. Malposition of the ETT may jeopardize airway protection or cause inadequate ventilation. It is therefore imperative to intubate a patient quickly and position the ETT correctly when a medical condition arises.

Various technologies have been developed to assist the placement of the endotracheal tube into the trachea. In a technique called direct laryngoscopy, a laryngoscope is used to obtain a direct view of the glottis and the endotracheal tube is then inserted to pass through the mouth, larynx, and vocal cords into the trachea under direct vision. Another technique uses flexible fiberoptic bronchoscopes to obtain indirect view of epiglottis and vocal cord through coated glass fiber to facilitate intubation. A recent technology, a video laryngoscope, incorporates a video camera at a tip of modified laryngoscope to further assist the visual verification of ETT placement.

The above technologies heavily rely on visual observation and the experience of the user. Despite the improved visibility by various techniques and extensive training, failed intubation occurs frequently. Further, intubation under direct or indirect visual observation is not always possible in clinical practice. For example, visual verification may be impossible under some medical conditions, such as unstable cervical spine, airway trauma, heavy airway secretion, bleeding, etc.

While intubation is frequently performed by highly trained medical professionals in a hospital setting, such as an emergency room, operation room, or intensive care unit, etc., it is also performed by paramedics or equivalent in non-hospital settings, such as battlefields, motor vehicle accident scenes, or various field medical emergencies. Lack of experienced medical professionals and lack of easily-operated intubation devices may make the life-saving procedure difficult with potential loss of life in both hospital settings and non-hospital settings.

SUMMARY

The inventor herein has recognized that it may be desirable to have an easily operated intubation device that can intubate a patient without solely depending on visual aids for the intubation. A system and method is provided for intubating a patient manually, semi-automatically or automatically via feedback from a trachea condition sensor. According to one aspect, an intubation device comprises a movable guide configured to guide an insertion of an endotracheal tube into a trachea of a patient, the guide having a guide extension and a guide tip; an external trachea identifier source external to the trachea and disposed on the patient during an intubation, wherein the trachea identifier source generates and transmits a signal; at least one trachea condition sensor disposed on the guide tip to detect the signal generated by the trachea identifier source; and a guide control device operatively coupled to the guide, the guide control device configured to move the guide into the trachea in response to the detected signal.

According to another aspect, an intubation device comprises a movable guide configured to guide an insertion of an endotracheal tube into a trachea of a patient, the movable guide having a guide extension and a guide tip; an external trachea identifier source disposed external to the trachea and on a body of the patient during an intubation, wherein the trachea identifier source generates a signal and transmits the signal toward the trachea; at least one trachea condition sensor disposed on the guide tip to detect the signal generated and transmitted by the trachea identifier source; and a guide control device operatively coupled to the guide and communicatively linked to the trachea condition sensor, the guide control device configured to process a detected signal from the trachea condition sensor to determine an opening of the trachea and direct an insertion of the guide into the trachea in response to the detected signal.

According to another aspect, a method of intubating a patient using an intubation device is provided. The intubation device includes a guide, at least one trachea condition sensor on a tip of the guide, and a guide control device configured to move the guide. The method comprises disposing an external trachea identifier source in a location external to a trachea of the patient; detecting signals transmitted from the external trachea identifier source using the trachea condition sensor; processing real time information from the detected signal of the trachea condition sensor to determine an opening of the trachea; and moving the guide in response to the processed real time information.

BRIEF DESCRIPTION OF THE DRAWINGS

FIG. 4 is a schematic diagram of the intubation device of FIG. 1, illustrating example components of the intubation device.

FIG. 5 is a flowchart illustrating an example method of intubating a patient automatically or semi-automatically using an intubation device according to an embodiment of the present disclosure.

FIG. 6 is a schematic illustration of an example user interface of an embodiment of the intubation device of FIG. 1 according to the present disclosure.

FIG. 8 is an exploded front view of a guide tip of an intubation device according to another embodiment of the present disclosure.

FIG. 9 shows a schematic view of a guide of an intubation device according to another embodiment of the present disclosure.

FIG. 10 illustrates another embodiment of an intubation device according to the present disclosure.

FIG. 11 is an exploded view of a guide tip of the intubation device of FIG. 10.

DETAILED DESCRIPTION

As described in more detail below, an intubation device of the present disclosure can correctly intubate a patient with or without visual assistants. For example, in some embodiments, the intubation device may comprise an intubation guide, a guide control system, an information processing center, and various accessories, such as a digital video system, a medication delivery system, a medical instrument conduit, a remote control module, etc. In some embodiments, an intubation guide may comprise an airway-specific sensor that can process real time trachea airway information continuously; a direction-seeking guide tip configured to react to the sensed and processed airway information; and a guide body that can extend and retract in response to sensed and processed airway information. In some embodiments, the intubation device may include a build-in digital video camera and conduits within the guide. In this way, the intubation device can have visual confirmation capability, medication delivery functionality and instrument insertion flexibility during the intubation.

Figure 1:
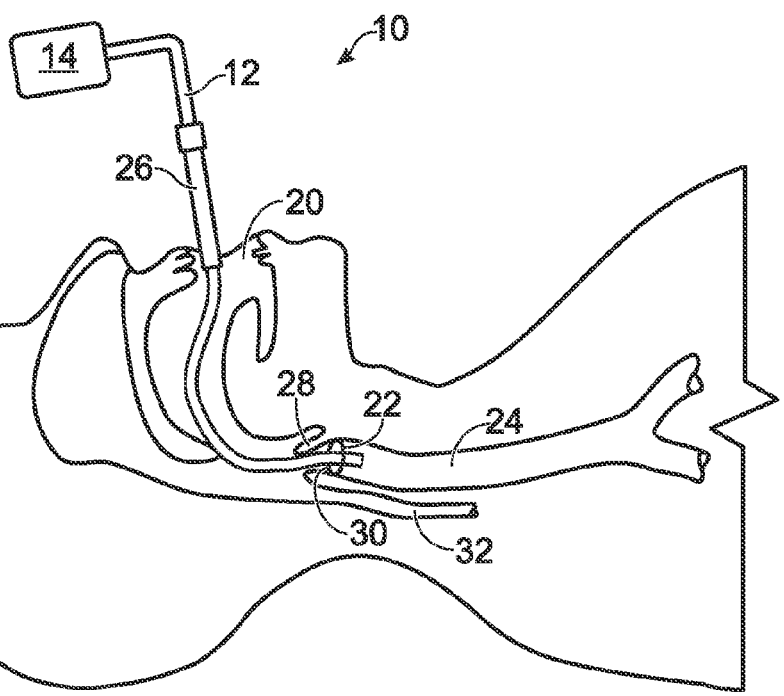
FIG. 1 shows a schematic view of an intubation device as used to intubate a patient.

FIG. 1 shows a schematic view of an example intubation device 10 in accordance with the present disclosure as used to intubate a patient. Intubation device 10 may include a guide 12 and a guide control device 14. Guide 12 may be adapted to pass through the patient mouth 20, vocal cord 22, and insert into trachea 24. Guide control device 14 may be configured to direct an insertion of guide 12. In some embodiments, guide device 14 may be configured for directional control of a guide tip and extension and/or retraction of a guide body in response to trachea airway information received from a trachea condition sensor or in response to the user's clinical decision. When it is determined that guide 12 is in trachea 24, an endotracheal tube 26 may be moved over guide 12 and into trachea 24. Then, guide 12 may be removed from trachea 24. Endotracheal tube 26 may remain in trachea 24.

FIG. 1 also illustrates possible paths during the guide placement. As shown in FIG. 1, epiglottis 28 and glottis 30 are in the front of vocal cord 22. Esophagus 32 is under trachea 24. Trachea is located anterior to esophagus 32. Trachea is an open tube-like cartilage structure while esophagus is normally collapsed in the absence of swallowing. Two cavities, trachea 24 and esophagus 32, are adjacent each other. Thus, guide 12 may be inserted into either trachea 24 or esophagus 32. As described below, intubation device 10 is configured to prevent the guide or tube being inserted into esophagus 32.

For example, intubation device 10 is configured to direct guide 12 into trachea 24 correctly based on at least one trachea condition. The trachea condition may be detected by a trachea condition sensor disposed on guide 12. In some embodiments, the trachea condition may be a unique natural or existing condition in trachea 24 including but are not limited to carbon dioxide ($CO_2$), oxygen, nitrogen, or air flow, etc. In some embodiments, the trachea condition may also be an artificial or introduced condition that is configured to distinguish trachea 24 from esophagus 32. The introduced trachea condition may include an introduced compound. The compound may be breathed, swallowed, drank or injected to the patient and then can be exhale via the lungs and the trachea. In some embodiments, the trachea condition may be a signal condition generated by a trachea identifier source. For example, the signal may include light, sound, magnetic field, electricity, etc. Trachea conditions will be described in detail below.

Intubation device 10 enables directional movements as well as advancing and withdrawing movement during insertion of guide 12 into trachea 24 in response to the detected trachea condition. In this way, intubation may be performed "blindly" without or with visual verification.

In addition, intubation device 10 may also be used as a confirmation device for correct ETT placement and proper position. For example, confirmation may be needed in certain circumstances, such as double lumen ETT placement and position, bronchial blocker placement and position, ETT exchange or after any suspected ventilation problems. In such circumstances, guide 12 may be reinserted into trachea 24 through endotracheal tube 26. Proper placement of endotracheal tube 26 may be reconfirmed by information from the trachea condition sensor. In some embodiments, the placement of endotracheal tube 26 may further be reconfirmed by a video image captured by a video camera on guide 12. Alternatively, confirmation of proper placement may be also performed by known methods, such as direct laryngoscopy, fiberoptic bronchoscopy, chest auscultation, and carbon dioxide detection.

Figure 2:
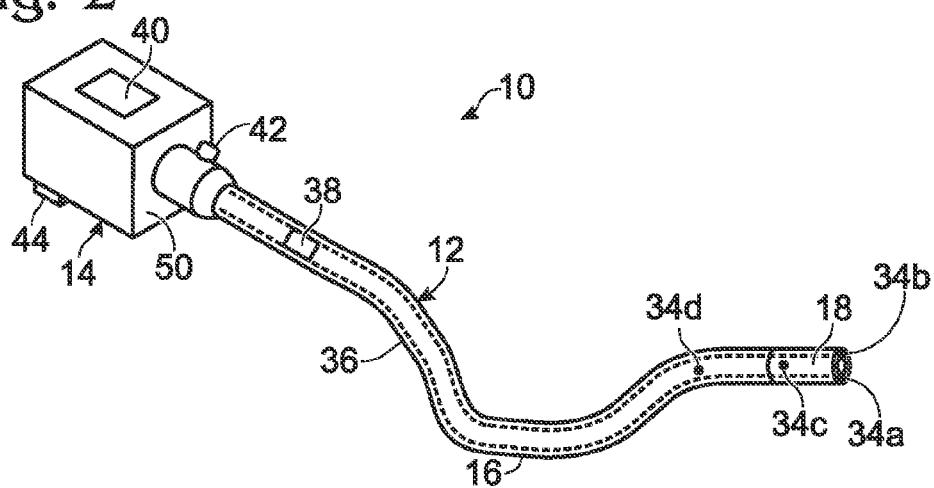
FIG. 2 is a perspective view of the intubation device of FIG. 1 according to an embodiment of the present disclosure.

FIG. 2 is a perspective view of an embodiment of the intubation device 10 in FIG. 1 according to the present disclosure. As shown in FIG. 2, intubation device 10 may comprise a guide 12, a guide control device 14, and at least one of trachea condition sensors 34a, 34b, 34c, 34d disposed on guide 12. In the depicted embodiment, guide 12 may include a guide extension 16 and a guide tip 18. Guide control device 14 may be configured to drive guide 12 in all directions into trachea 24 in response to detected trachea conditions in any suitable manner. For example, guide 12 may be inserted into the trachea manually, semi-automatically or automatically in response to information from the trachea condition sensors. Additionally, or alternatively, control device 14 may be configured to override the automated guide movements at a user's discretion.

Trachea condition sensors, 34a, 34b, 34c, 34d may be configured to detect trachea conditions. As described above and will be described in detail below, a trachea condition may be any condition that distinguishes the trachea from the esophagus. Information from the trachea condition sensor may assist correct insertion of guide 12 and/or confirm placement of endotracheal tube 26.

In the depicted embodiment, trachea condition sensors 34a and 34b are disposed on an end of guide tip 18, trachea conditions sensor 34c is disposed on a side of guide tip 18, and trachea condition sensor 34d is disposed on a side of guide extension 16. It should be appreciated that the trachea condition sensor may be disposed on any suitable position of guide 12 to detect the trachea condition and generate a reliable information that distinguishes the trachea from the esophagus.

While four trachea sensors are shown in FIG. 2, it should be appreciated that any number of trachea condition sensors may be used. For example, only one trachea condition sensor may be disposed on guide 12. As an alternative, guide 12 may include two or three trachea condition sensors. As another alternative, more than four trachea condition sensors may be employed in an intubation device.

Further, any combination of trachea condition sensors may be used. For example, sensors 34a and 34b may detect existing trachea conditions, sensor 34c may detect introduced trachea conditions, and sensor 34d may detect signal trachea conditions. Alternatively, selected sensors may detect the same trachea condition at different levels. For example, trachea condition sensors 34a and 34b may be $CO_2$ sensors that detect $CO_2$ at different concentration levels, trachea condition sensor 34c may be a pressure sensor or a flow rate sensor, and trachea condition sensor 34d may be a light sensor.

Continuing with FIG. 2, guide 12 may be made from flexible, semi-flexible or rigid materials. In some embodiments, guide 12 may be configured to be in a form similar to intubation stylets known in the art. However, it should be appreciated that guide 12 may be formed in other configurations. While guide 12 may comprise guide extension 16 and guide tip 18 as two portions as shown in FIG. 2, guide 12 may be formed as an integrated part. Further, guide extension 16 and guide tip 18 may be made from the same material or different materials.

Further, guide 12 may assume any suitable configuration adapted for an automated or semi-automated intubation device or a manual insertion following information from the trachea condition sensors. For example, guide 12 may be configured to be moved semi-automatically, i.e., moved through activation of movement control actuators by a user or to be moved automatically, i.e., moved through execution of a software program stored in the guide control device 14. In one example, guide movements may include motions of guide tip 18 in all directions in response to detected trachea conditions and motions of guide extension 16 to follow the guide tip 18. In some embodiments, to facilitate the guide movement, guide 12 may include a plurality of flexible cords 36. Alternatively, guide 12 may include a single cord or a backbone to facilitate its movements instead of a plurality of cords 36. Guide 12 may also include guide actuator 38 that enables the desired movements as described herein. While guide actuator 38 is shown to be disposed on guide 12, guide actuator 38 may also be disposed in a house of guide control device 14 or in any suitable locations. It should be noted that guide 12 may include any suitable feature that enables the desired movements and guide 12 may be adapted to any specific mechanism that moves the guide.

Additionally, intubation device 10 may include a set of varying sized guides adapted to fit various types of patients, such as adults and children. Guide 12 may be detachably coupled to control device 14 by a coupler, such that guide 12 may be changed to fit for the requirements for different patients.

Further, it should be appreciated that guide 12 may be configured to be used as an endotracheal tube. For example, guide 12 may include a hollow tube. As the guide 12 is inserted into the trachea, guide 12 may be detached from guide control device 14 and remain in trachea 24 to provide required airway management.

To operate intubation device 10, a user interface 40 may be included. In some embodiments, user interface 40 may include a display to present information, such as intubation data. The information or intubation data may include indicia, such as level, intensity, or patterns of a trachea condition. In a manually-operated intubation device, a user may insert guide 12 and adjust its positions according to the displayed trachea conditions. In some embodiments, user interface 40 may include a user input device such as actuators configured to activate automated movements of the guide. For example, in a semi-automatic intubation device, the user may activate appropriate actuators to move the guide in corresponding directions based on displayed trachea conditions. In an automatic intubation device, activation of one or more actuators may initiate the guide insertion and perform the intubation automatically. Relevant information may also be displayed on user interface 40 to enable monitoring and/or controlling of the intubation process. It should be appreciated that the user interface may be configured to include one or more displays in any suitable manner to accommodate specific operating mechanisms of intubation device 10.

Additionally, or alternatively, intubation device 10 may also include a multiple function port 42 configured to administrate medicines to the patient as guide 12 moves into the trachea. As an example, the medicine may include local anesthetics, inhalation anesthetics, $O_2$ or bronchodilators. Alternatively, the multiple function port 42 can be used as a conduit for instruments to perform tissue biopsy, laser treatment and other diagnostic or therapeutic procedures.

Further, intubation device 10 may include a power supply 44 that provides power required by the electronic and/or mechanical components of the intubation device. In some embodiments, power may be supplied from an external power source, such as an AC outlet or external power source or combination of the two power sources. Alternatively, power supply 44 may include one or more batteries in a battery compartment of power supply 44. As yet another alternative, power supply 44 may include a solar cell configured to gather energy from ambient light.

Figure 3:
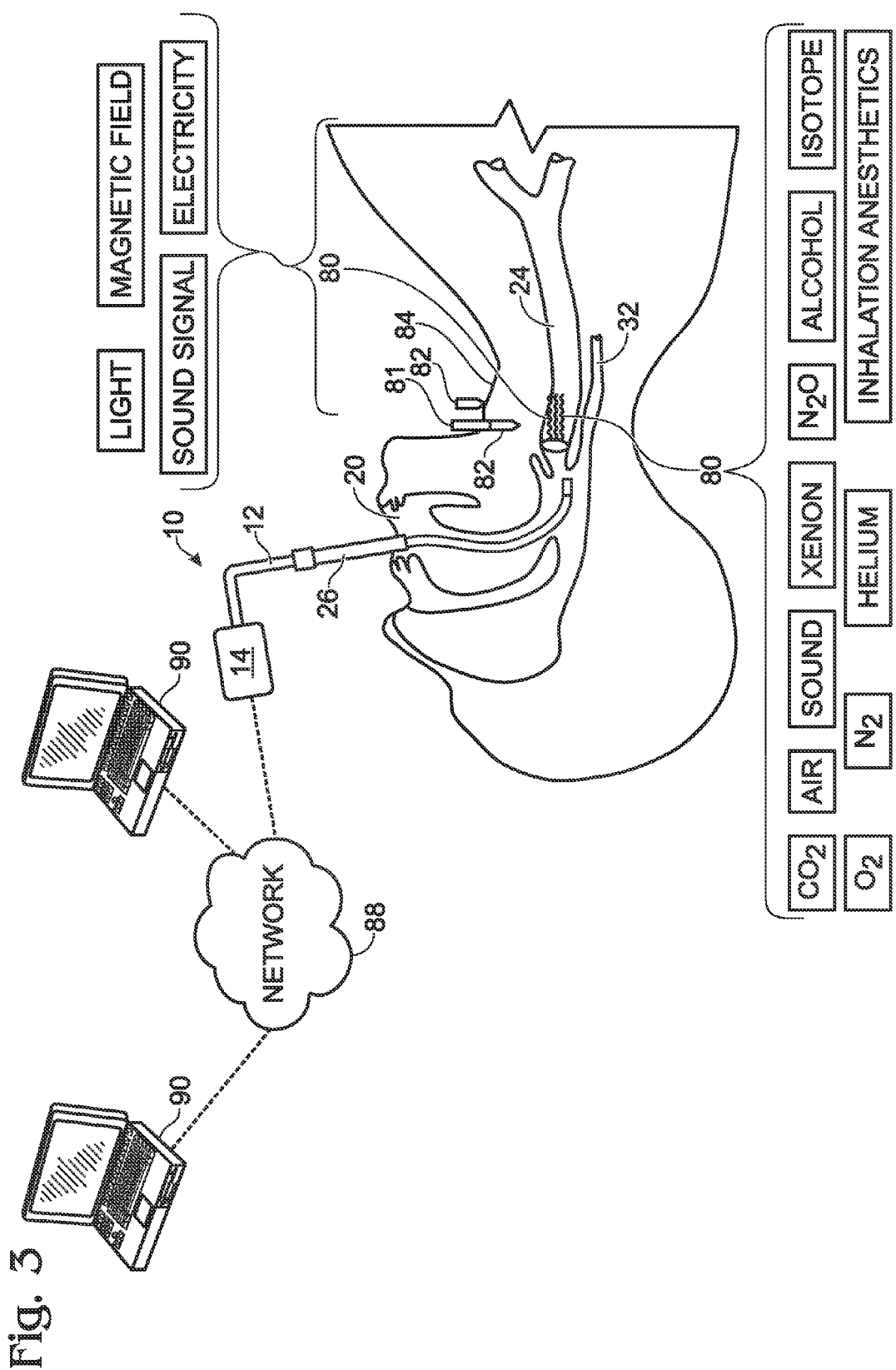
FIG. 3 is a schematic view of the intubation device of FIG. 1 as used to intubate a patient, illustrating trachea conditions and trachea identifier sources to generate trachea conditions.

FIG. 3 is a schematic view of intubation device 10 as used to intubate a patient, illustrating trachea conditions and trachea identifier sources that generate trachea conditions. Trachea conditions may include any identifiable characteristic that differentiates trachea 24 from esophagus 32 because the characteristic is either only present in the trachea or is present in different magnitudes or patterns in the trachea and the esophagus. As shown in FIG. 3, example trachea conditions 80 may include, but are not limited to $CO_2$, oxygen ($O_2$), nitrogen ($N_2$), helium, air flow, positive or negative pressure, pressure change, air flow, inhalation anesthetics (e.g., desflurane, isoflurane, sevoflurane), Xenon, nitrous oxide ($N_2O$), sound including ultrasound, alcohol, isotope, light, magnet, and electricity, etc.

As described above, a trachea condition or trachea-specific condition may include an existing trachea condition that differentiates trachea from esophagus. The existing trachea condition may include characteristics naturally existing in the trachea. In some embodiments, the existing trachea condition may be considered as natural trachea condition. For example, $CO_2$ is exhaled from the lungs and is naturally present in the trachea but is absent from the esophagus. Thus, the trachea condition may be $CO_2$ and a trachea condition sensor may be a $CO_2$ sensor configured to detect the presence of $CO_2$. In some embodiments, the $CO_2$ sensor may be configured to detect $CO_2$ concentrations at or above an atmospheric level. It should be appreciated that the $CO_2$ sensor may be any suitable $CO_2$ sensor that can detect $CO_2$ qualitatively or quantitatively and can respond to the $CO_2$ concentration variations or $CO_2$ gradients quickly.

Similarly, oxygen and nitrogen exist naturally in the trachea. Thus, the trachea condition may be oxygen or nitrogen and the trachea sensor may be an oxygen sensor or a nitrogen sensor.

In another example, air flow in the trachea may be a unique identifier of the trachea to distinguish the trachea from the esophagus. The trachea condition may be airflow and air pressure. The trachea condition sensor may be a flow rate meter that measures air movement or amount of air in the trachea. The trachea condition sensor may also be a pressure sensor that measures the pressure or pressure changes in the trachea. In some embodiments, as an example, an automatic intubation device for a spontaneous ventilation patient may be configured in such a manner that a patient's respiratory movement initiates and guides the insertion of guide 12 in response to an intensified signal from air flow or pressure sensors. It should be noted that an air flow rate meter and a pressure sensor may be any suitable sensor that can detect the desired levels of air flow and air pressure (either positive or negative pressure).

In yet another example, an existing trachea condition may be sound in the trachea generated by the air movement, air turbulence and phonation (vocal cord is the beginning of the trachea). Thus, any suitable sound sensor may be used as a trachea condition sensor.

In addition, the trachea condition may be an introduced or artificial condition foreign to the trachea. For example, a compound or a tracer may be introduced into the patient by inhalation, digestion or injection. Exhaling the compound or the tracer from the lungs may create a trachea-specific condition. As an example, the compound may include intravenous alcohol, helium, inhalation anesthetics, Xenon, or $N_2O$, etc. The trachea condition sensor or compound detecting sensor may include a sensor to detect the presence and concentration of one or more such compounds or tracers.

In another example, an introduced compound may be spiked with a trace amount of an isotope, such as $H_3O$. The isotope may be detected by an isotope sensor.

It should be noted that the introduced tracer may be any suitable compound or substance that can be introduced to the patient and its presence in the trachea or around the entry point to the trachea is detectable by a sensor. The substance may be in a state of gas, liquid, or solid. The compound may have minimum side effect to the patient.

In addition to the existing and introduced trachea conditions, a third type of trachea condition may be a signal trachea condition. In some embodiments, the signal trachea condition may be a detectable signal or trachea identifier generated by a trachea identifier source 82. Because of different anatomical locations of trachea 24 and esophagus 32 (trachea 24 is located anterior to esophagus 32) and different geometric structures around entries to the trachea and the esophagus (the trachea is an open tube-like cartilage structure verse esophagus which is normally collapsed in the absence of swallowing). The signal transmitted to the trachea or around the trachea may have different intensities or patterns than those in the esophagus. Thus, detected signal may provide information that distinguishes the trachea from the esophagus. In some embodiments, the trachea identifier may be in a form of energy. In one example, trachea identifier source 82 may be a light source. Trachea identifier source 82 may be configured to generate any suitable light, such as visible light, ultraviolet, infrared, laser, etc. Trachea identifier source 82 may also include light emitting diodes (LEDs). The trachea condition sensor may be a light sensor.

In another example, trachea identifier source 82 may include a sound device to generate sound. The sound device may be configured to create and send sound in any suitable decibel level to trachea 24. For example, the sound may be audible sound and ultrasound. The trachea condition sensor may be a sound detector.

In yet another example, trachea identifier source 82 may comprise a magnetic source configured to generate a magnetic field in trachea 24. The magnetic source may include any suitable source, such as a permanent magnet or electric magnet. The trachea sensor may be a magnetic sensor.

In still another example, an electrode pair may generate a detectable electric signal. For example, trachea identifier source 82 may include a first electrode that forms an electrical cell together with a second electrode disposed on guide 12. An electrical signal may be generated when both first electrode and second electrode are in contact with the patient's body. A specific range of electrical impedance may exist when guide 12 contacts trachea 24. The range may distinguish trachea 24 from esophagus 32. Thus, it is possible to identify trachea 24 by a measurement of electric signals, such as a voltage or a current generated in the cell. It should be appreciated that, in some embodiments, the first electrode on guide 12 may be employed as a trachea condition sensor.

Continuing with FIG. 3, trachea identifier source 82 may be disposed in a position that is adjacent to trachea 24. In some embodiments, trachea identifier source 82 may be disposed on the patient's neck 84 above trachea 24. In some embodiments, trachea identifier source 82 may be disposed inside the patient body and adjacent to trachea 24. For example, trachea identifier source 82 may be mounted on a needle-like structure 81 and embedded into neck 84 during the intubation.

Alternatively, trachea identifier source 82 may be disposed on guide 12. As guide 12 is inserted into the trachea, the signal or the trachea identifier transmitted to trachea 24 may be different from the signal transmitted to esophagus 32 when guide 12 is inserted into esophagus 32, thus distinguishing the trachea from the esophagus.

FIG. 3 also shows an alternative embodiment of intubation device 10. As shown in FIG. 3, intubation device 10 may be connected to a network 88. Intubation device 10 may be configured to connect to network 88 and enable commutations with a plurality of computing devices 90. Computing device 90 may be located remotely to a location where an intubation is performed. Intubation device 10 and computing device 90 may be connected to the network 88 through wire or wireless connections.

Connections between intubation device 10 and computing device 90 allow the intubation to be monitored and controlled remotely. For example, information on operations of intubation device 10, i.e., intubation data (e.g., detected trachea conditions, positions of guide, etc.) may be sent to computing device 90. In turn, a user of intubation device 10 may receive instructions from network 88. In this way, the intubation may be monitored, controlled and/or supervised. Communications between the intubation device and network may be useful when the intubation is performed at non-hospital settings, such as emergency sites or battlefields or when the intubation is performed by less-trained personnel. For example, the intubation may be performed at an emergency site and may be monitored by a doctor at a hospital. In another example, the intubation may be performed at one location and may be supervised by a person using computing device 90 at the same location. Moreover, a user may use computing device 90 to operate and control the intubation remotely. In one embodiment, computing device 90 may function as guide control device 14 to perform various operations, such as control guide movements, etc, i.e., enable control of guide control device 14. For example, the intubation may be initiated at one location and may be performed by a doctor in another location.

FIG. 4 is a schematic diagram of intubation device 10, illustrating example components of the intubation device. As illustrated in FIG. 4, guide control device 14 may include a user interface 40 and a controller 50. User interface 40 may include a user input device 52 to activate and operate intubation device 10. Further, user interface 40 may include a display 54 to present information on an operation of intubation device, such as intubation data (e.g., detected trachea conditions, etc.). Display 54 may also be presented on one or more networked computing devices 90 as described in regards to FIG. 3.

Controller 50 may include a processor 56, a memory 58, and a communication interface 60. Processor 56 and communication interface 60 may be linked by a bus to memory 58. Controller 50 may also be configured to communicate with trachea condition sensor 34 via communication interface 60. In some embodiments, memory 58 may include both non-volatile and volatile memory, and programs or algorithms may be stored in non-volatile memory and executed by the processor using portions of volatile memory to accomplish the operations described herein.

In some embodiments, the intubation may be performed manually. As described above, trachea condition sensor 34 may be disposed on guide 12. When intubation device 10 is activated, a user may insert guide 12 into the patient's mouth or nose and then adjust a position of guide 12 based on displayed trachea condition information (e.g., on display 54) received from the trachea condition sensors. Additionally, or alternatively, the user may insert guide 12 at his/her discretion.

In some embodiments, guide 12 may be configured to move semi-automatically or automatically. Intubation device 10 may further comprise a motion manipulation unit 62 operatively coupled to guide 12 and controller 50. Controller 50 may be configured to communicate with trachea condition sensor 34 and motion manipulation unit 62 via communication interface 60 to perform various operations described herein.

Motion manipulation unit 62 may be configured to cause desired movements of guide 12 automatically, semi-automatically and/or manually and may include one or more motors, drives, etc. In one example, desired movements may include, but are not limited to forward movement, backward movement, movements in any direction or any angle relative to a guide position. The guide's motion may include, but is not limited to linear motion, 360° rotation or combinations thereof. In some embodiments, guide tip 18 may be configured to perform steering motions, such as moving in any direction and guide extension 16 is configured to extend and/or retract following guide tip 18. Motion mechanisms to facilitate such movement of the guide may include guide actuators, gears, or any suitable feature or connector that enables the various movements described herein.

In some embodiments, the guide's movements may be fully automated. For example, controller 50 may be configured to include a program or an algorithm to move guide 12 in response to a trachea condition detected by trachea condition sensor 34. In some embodiments, when guide 12 is inserted into a patient's mouth or nose and intubation device 10 is activated, guide tip 18 may be automatically moved forward and its position may be automatically adjusted in any directions (e.g., 360° degrees) relative to the position of guide 12 to search for or trace the trachea condition. Guide extension 16 may follow the guide tip 18. As a result, the guide may appear to perform a snake-like movement. For example, guide tip 18 may act like a snake head to steer and lead guide 12. Guide extension 16 may perform the snake-like motions and follow the guide tip into the trachea. It should be appreciated that guide 12 may be configured to perform any suitable movements to search for the trachea and move into the trachea. Further, it should be noted that any suitable known method known in the art may be used to enable the automated movements.

In some embodiments, the guide movements may be performed semi-automatically. For example, the movements may be actuated through user input device 52. User-directed movements such as forward, backward, movements in any direction relative to the guide position may be actuated by a user using corresponding actuators on user input device 10.

Additionally, the use-directed movements and/or automated movements may be guided by information on the trachea condition that is presented on display 54. Alternatively, the movement may be activated or controlled by a user using computing device 90 via a network connections.

Additionally, or alternatively, guide control device 10 may be configured to permit the user interaction during the automated or semi-automated intubation process. For example, the automated guide movement may be overridden by a user's input at any time. In this way, the intubation may be further refined by the user.

FIG. 5 is a flowchart illustrating an example method 100 to intubate a patient automatically or semi-automatically using an intubation device according to one embodiment of the present disclosure. First, at 102, method 100 includes activating at least one trachea condition sensors. Next, at 104, method 100 includes moving a guide or introducing the guide. At 106, method 100 determines whether a trachea condition is detected by a trachea condition sensor. The trachea condition may be detected when a first trachea condition threshold is exceeded. The first trachea condition threshold may be a background level of a trachea condition around entry points of trachea 24 and esophagus 32. For example, where the trachea condition is $CO_2$, the first threshold may be a $CO_2$ level at atmosphere. In another example, where the trachea condition is pressure, the first threshold may be an atmosphere pressure. The first threshold may be any suitable value for a specific trachea condition. Alternatively, the first threshold may be set to zero by normalizing a background level.

If the trachea condition is not detected by the trachea condition sensor (i.e., the level of the trachea condition is not above the first trachea condition threshold), then at 108, method 100 includes adjusting the direction of the guide. As described above, in some embodiments, adjusting the direction of the guide may be accomplished by moving a guide tip in any direction or any angle relative to a guide position or a moving path. Further, the adjustment may be performed while the guide is moved forward into the trachea. Alternatively, the guide may be retracted and redirected from a position where the trachea condition is not detected. The adjustment may continue until the trachea condition is detected.

If the trachea condition is detected by the trachea condition sensor (i.e., the level of the trachea condition is above the first trachea condition threshold), then at 110, method 100 includes moving the guide toward the trachea condition.

In some circumstances, indicia or signals for the trachea condition are greater in the lungs and trachea 24 than those around an entry point to the trachea. Thus, in some embodiments, the guide may be moved forward in a direction that has an increased gradient or a higher level of trachea signal or indicia for the trachea condition. For example, the guide may be moved toward a higher level of $CO_2$, higher concentration of an introduced compound, higher air flow rate, or greater energy intensity, etc. However, in some embodiments, the guide may be moved toward a decreased gradient of the trachea condition. For example, the guide may be moved toward a decreased pressure or a negative pressure when the trachea condition is air pressure and the patient is taking a deep breath.

Next, at 112, method 100 determines whether the indicia or level of the detected trachea condition is greater than a second trachea condition threshold and/or remains a constant or in a constant range for a predetermined time interval. Since the trachea condition is a unique identifier for trachea 24, indicia for the trachea condition may be in a substantially constant level in trachea 24. Step 112 may determine whether the guide tip is positioned in trachea 24.

If the indicia of the trachea condition are greater than the second trachea condition threshold and/or consistent for a predetermined time interval, at 114, method 100 includes stopping guide movement. Then, endotracheal tube may be slipped over the guide and inserted into the trachea at 116.

The method described above enables an automatic or semi-automatic movement of the guide in response to the trachea condition detected by the trachea condition sensor. Thus, the position of the guide is continually adjusted through feedback from the trachea condition sensor. In this way, the guide can be accurately inserted into trachea 24.

Note that various steps or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated steps or functions may be repeatedly performed depending on the particular strategy being used. Further, the described steps may graphically represent code to be programmed into the computer readable storage medium in guide control device.

FIG. 6 is a schematic illustration of an example user interface of an embodiment of an intubation device 10 according to the present disclosure. As shown in FIG. 6, a user interface 40 may include a user input device 52 and a display 54. In some embodiments, user input device 52 may include actuators 70 (such as a button, switch, etc.) to activate an operation of intubation device 10. For example, actuators 70 may selectively activate a trachea condition sensor for a manually-operated intubation device. In another example, actuators 70 may activate an automated or semi-automated intubation process. Further, actuators 70 may be configured to select proper operating mode or operating parameters. Additionally, actuators 70 may be configured to override an automated operation at the user's discretion such that the user may control the intubation due to some unexpected medical conditions.

Additionally, or alternatively, user input device 52 may include actuators 72 to enable various movements of guide 12 as described above. For example, actuators 72 may actuate and control movements, such as forward movement (FW), backward movement (BW), or movement in any direction (i.e., any direction in three-dimensional space).

It will be appreciated that the actuators described above may be either soft buttons displayed on the graphical user interface of the guide control device 14, or hard controls physically located on the device, such as buttons, joystick, trackball, touch-sensitive pad, etc. Alternatively, it will be appreciated that touch sensitive screen having touch selectors may be employed as described above, and/or a non-touch sensitive screen may be utilized and a user input device such as mouse or keyboard may be used to input data and/or actuate buttons.

User interface 40 may also include a display 54 to present information on the operation of intubation device 10. In one example, information may include the trachea conditions detected by the trachea conditions sensors. For example, display 54 may present a level of a trachea condition presented in either graphic or text format 74 as shown in FIG. 6. Further, display 54 may show status of the operation. For example, display 54 may show a message indicating that trachea condition is detected, or a message indicating that guide is in the trachea. Display 54 may present any suitable information to assist the user to operate intubation device 10.

Additionally, or alternatively, user interface 40 may include an image display 76 to present an image captured by a video disposed on the guide tip. In one example, the image may be a view around the entry point to the trachea. In another example, the image may relay real time movement of the guide during intubation. The intubation process can be captured, stored and printed according to a user's discretion.

Additionally, or alternatively, in some embodiments where intubation device 10 is connected to a network, user interface 40 may include a message display 78 configured to present a message received from the network. In one example, information may include an instruction on how to operate the intubation device or intubate the patient.

Figure 7:
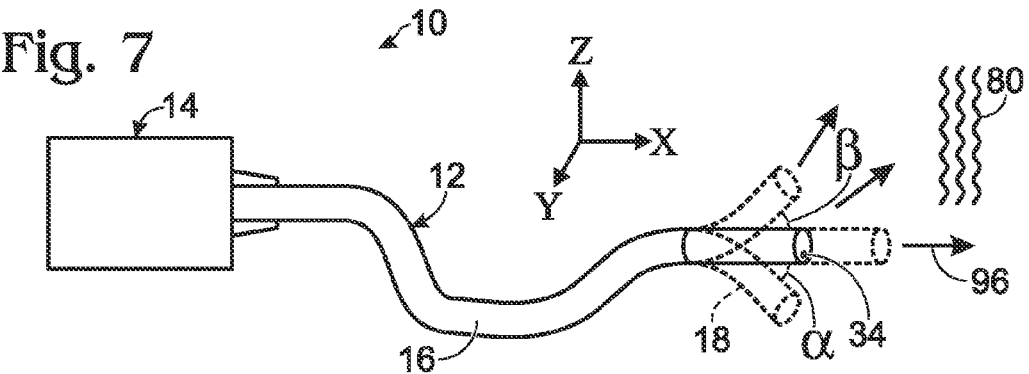
FIG. 7 is a schematic illustration of guide motions in response to a trachea condition.

FIG. 7 is a schematic illustration of guide motions in response to detected trachea conditions. As shown in FIG. 7, guide tip 18 may move toward the trachea condition 80. Guide tip 18 may move in any direction as indicated by x, y, z ordinates. Further, guide tip 18 may move at any angle, such as α or β and guide extension 16 may move forward and/or retract following the lead of guide tip 18 automatically or based on the user's inputs or instructions.

The system and methods of the present disclosure may make intubation easy, fast, and accurate. For example, intubation may be performed based on a real time trachea condition detected by a trachea condition sensor using an intubation device. Thus, the trachea can be located accurately. The intubation device may be suitable for both routine and difficult intubations. Further, since the trachea is detected by the trachea condition sensor, the intubation can be performed without solely relying on visual observation. Moreover, the intubation device may be suitable for some difficult intubations where visual verification of insertion or placement of the endotracheal tube or guide to the endotracheal tube is not possible.

In some embodiments, the intubation device can be automated based on information from the trachea condition sensor. The automation enables controlled guide movements. For example, the guide's movement, such as a distance of every move, speed, or moving direction may be programmed to desired values. Thus, insertion may be performed in a smooth and controlled manner and may be completed accurately in a short period of time.

In addition to reduce potential errors in intubation, the intubation device also enables easier intubation. Thus, intubation may be successfully performed as a life-saving procedure in a variety of settings, including emergency sites and battlefields where highly trained medical professionals may not be available.

FIG. 8 is an exploded front view of a guide tip of an intubation device 200 according to another embodiment of the present disclosure. Similar to the intubation device described above, intubation device 200 may include a guide tip 218 and a guide control device. In the depicted embodiments, a plurality of trachea conditions sensors 234a, 234b, and 234c are disposed on an end of guide tip 218. The trachea condition sensors may be different types of sensors to detect different types of trachea conditions. For example, sensor 234a may detect an existing trachea condition sensor 234b may detect an introduced trachea condition, and sensor 234c may detect a signal trachea condition. Any number and combination of sensor types are possible and contemplated in the present disclosure.

Optionally, or additionally, a position sensor 250 may be disposed on guide tip 218 to determine a position of guide tip 218 as a guide moves toward and inside the trachea. Information from position sensor 250 may be used by the guide control device to adjust movements of the guide to provide feedback control of the guide tip. Position sensor 250 may be any suitable sensor such as a string potentiometer or a hall effect sensor. In one example, position sensor 250 may be used as a measuring device.

The guide may be of any conformation. For example, as shown in FIG. 8, the guide may include a conduit or delivery conduit, such as in a form of a hollow tube with channel 252 that allows the delivery of medicine, inhalation anesthetics, oxygen, the passage for surgical instruments (such as biopsy cable), laser fiber, or suction. Further, the guide may include cords or cables as described in detail in regards to FIG. 9. Moreover, the guide may provide a link for fiber optic cables, etc.

Additionally, intubation device 200 may include a visual assist to verify or confirm the insertion of the guide. In one example, the visual assist may include a video camera 246 and a light source 248 disposed on guide tip 218. Light source 248 may generate light for capture of an image by video camera 246 and light may be transmitted via fiber optics by a light generate source. The visual assist allows the capture of images in a view of the guide tip. In some embodiments, the view may include a view in front of guide tip 218, a view surrounding guide tip 218 and a view of guide movements.

The additional video feature allows the insertion to be viewed by the user to monitor and verify the insertion. Thus, in some embodiments, a user may be able to more easily control the insertion process by observing the guide tip passing through the vocal cord, moving into the trachea, and inserting into a targeted body part.

Optionally, in some embodiments, intubation device 200 may be connected to a network. As described above, connection of intubation device 200 with a network enables communications on intubation process or intubation data between the intubation device and a computing device connected to the network. The additional video feature further permits communications on captured images or intubation images. The intubation data and intubation images may be displayed on the computing device so that the insertion may be viewed, operated, controlled, and/or manipulated by a third party.

FIG. 9 shows a schematic view of a guide of an intubation device 300 according to another embodiment of the present disclosure. Guide 312 may include a guide extension 316 and a guide tip 318. Guide 312 may also include trachea condition sensors 334a, 334b, and 334c. In the depicted embodiment, trachea sensors 334a and 334b are disposed on an end of guide tip 318. Trachea sensor 334c is disposed adjacent to guide tip 318 and spatially apart from guide tip 318.

Guide 312 may assume various configurations to facilitate automatic movements based on specific motion mechanisms. For example, guide 312 may include one of the features illustrated at A, B, and C. In some embodiments, guide 312 may comprise an extendable section or retractable section A. In some embodiments, guide 312 may include a section B having individual segments 360. Individual segments 360 may be operatively coupled together to provide certain degree of rigidity and flexibility to facilitate desired movements. In some embodiments, guide 312 may include a section C having a plurality of disks 362 connected by a plurality of cords 364. Again, section C may enable and facilitate desired movements. Although four cords are shown in FIG. 9, it should be noted that any number of cords may be used.

The features described above may enable a snake-like movement of the guide. It should be noted that any one of the sections A, B, and C may extend only a portion of the guide or may extend a substantial length of the guide. Alternatively, guide 312 may include one or more of the sections A, B, C, or other motion enabling section or guide 312 may include any combination of section A, B, C, or other motion enabling sections.

Also shown in FIG. 9, a coupler 368 is configured to couple guide 312 to the guide control device mechanically and electrically. In some embodiments, guide 312 may be detachably coupled to guide control device so that guide 312 may be changed to suit for requirements for different patients.

FIG. 10 illustrates another embodiment of an intubation device 400 according to the present disclosure. An exploded front view of a guide tip 418 of intubation device 400 is shown in FIG. 11. It should be appreciated that intubation device 400 may be used for various medical procedures in addition to intubation. In some embodiments, intubation device 400 may be used to assist a medical procedure such as delivery of medicine, etc. In other embodiments, intubation device 400 may perform a medical procedure by an insertion of a medical instrument 456 into a patient's body via a patient's trachea.

As shown in FIG. 10, intubation device 400 may include a guide 412 and a guide control device 414. Guide control device 414 may include a user interface 440. As shown in FIG. 11, intubation device 400 may also include trachea condition sensors 434a and 434b. As described above, trachea condition sensor may detect an existing trachea condition, an introduced trachea condition, or a signal trachea condition. Intubation device 400 may enable an insertion of guide 412 based on trachea condition detected by trachea condition sensors 434a and 434b.

Intubation device 400 may also include a multiple functional port 442. In some embodiments, multiple functional port 442 may be configured to administrate medicines to the patient. In some embodiments, multiple functional port 442 may be used as an entry to insert medical instrument 456 into guide 412. It should be noted that multiple functional port 442 may be positioned at any suitable location of intubation device 400.

As shown in FIG. 11, intubation device 400 may also include a conduit 458. In some embodiments, the hollow tube of guide 412 may be used as conduit 458. In some embodiments, conduit 458 may be used to deliver medicine.

In some embodiments, conduit 458 may be used as a passage for medical instrument 456. Medical instrument 456 attached to a cable or a connector 460 may be positioned into conduit 458 through multiple functional port 442. Medical instrument 456 may be used to perform various medical procedures, such as a tissue biopsy, laser treatment, diagnostic procedure, therapeutic procedure, etc.

It should be appreciated that conduit 456 may be a separate tube coupled to guide 412. Further, it should be noted that a plurality of conduits may be coupled to guide 412 for particular medical procedures.

Additionally, in some embodiments, intubation device 400 may include a visual assist to verify or confirm the insertion of guide 412. In one example, the visual assist may include an image capture device 446, such as a video camera, or a still camera. The visual assist may further include a light source 448 to provide light for image capture device 446. In the depicted embodiment, video camera 446 and light source 448 are disposed on guide tip 418 and adjacent to each other. Light may be transmitted to light source 448 through a light generation source 450. Light source 448 and light generation source 450 may include any suitable light producing device, such as fiber optics.

The visual assist allows an image in a view of guide tip 418 and guide movements to be captured by video camera 446. A video attachment 452 and an eye piece 454 may be included to allow the user to view the captured images.

Optionally, in some embodiments, intubation device 400 may be connected to a network such that intubation data and intubation images may be displayed on a computing device connected to the network. In this way, the insertion may be viewed, operated, controlled, and/or manipulated by a third party.

It will be appreciated that the configurations and routines disclosed herein are exemplary in nature, and that these specific embodiments are not to be considered in a limiting sense, because numerous variations are possible. The subject matter of the present disclosure includes all novel and nonobvious combinations and subcombinations of the various systems and configurations, and other features, functions, and/or properties disclosed herein.

The following claims particularly point out certain combinations and subcombinations regarded as novel and non-obvious. These claims may refer to "an" element or "a first" element or the equivalent thereof. Such claims should be understood to include incorporation of one or more such elements, neither requiring nor excluding two or more such elements. Other combinations and subcombinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An intubation device, comprising:
a movable guide configured to guide an insertion of an endotracheal tube into a trachea of a patient, the guide having a guide extension and a guide tip;
an external trachea identifier source external to the trachea and disposed on the patient during an intubation, wherein the trachea identifier source transmits a signal of a trachea condition;
a plurality of trachea condition sensors disposed on the guide tip comprising at least a sensor to detect an existing condition, a sensor to detect an introduced trachea condition and a sensor to detect the signal of the trachea condition; and
a guide control device for insertion of the guide into the trachea in response to at least one of the signal of the trachea condition, the existing condition, and the introduced trachea condition.

2. The intubation device of claim 1, wherein the guide tip is configured to move in x, y, z space in response to trachea conditions detected by the plurality of trachea condition sensors.

3. The intubation device of claim 2, wherein the guide control device includes a processor operatively coupled to the guide and configured to provide intubation data for display based on the plurality of trachea condition sensors.

4. The intubation device of claim 3, where the guide control device is configured to be manually operated based on the display of the intubation data.

5. The intubation device of claim 4, wherein the processor is configured to enable a user to override an automated motion of the guide control device.

6. The intubation device of claim 1, where the guide control device is configured to semi-automatically move the guide in response to at least one of the detected signal of the trachea condition, the existing trachea condition, and the introduced trachea condition.

7. The intubation device of claim 1, wherein the signal of the trachea condition is at least one of a light source, a sound generating source, a magnetic source, and an electrical source.

8. The intubation device of claim 7, wherein the light source is an invisible light source.

9. The intubation device of claim 7, wherein the sound generating source is an inaudible sound generating source.

10. The intubation device of claim 1, wherein the plurality of trachea condition sensors comprises at least one of a light sensor, a sound detector, a magnetic sensor, and a meter to measure a voltage or a current.

11. The intubation device of claim 1, wherein the plurality of trachea condition sensors comprises at least one of $CO_2$ sensor, $O_2$ sensor, $N_2$ sensor, compound detecting sensor, and/or airflow sensor.

12. The intubation device of claim 1, further comprising a video camera disposed on the guide tip.

13. The intubation device of claim 1, wherein the external trachea identifier source is not penetrating a front neck and the guide control device guides insertion into the trachea in response to the signal of the trachea condition.

14. An intubation device, comprising:
a movable guide configured to guide an insertion of an endotracheal tube into a trachea of a patient, the movable guide having a guide extension and a guide tip;
an external trachea identifier source configured to be disposed on a front neck of a patient during an intubation, wherein the trachea identifier source generates a signal of a trachea condition and transmits the signal of the trachea condition toward the trachea;
a plurality of trachea condition sensors disposed on the guide tip comprising at least a sensor to detect an existing trachea condition, a sensor to detect an introduced trachea condition and a sensor to detect the signal of the trachea condition; and
a guide control device operatively coupled to the guide and communicatively linked to the plurality of trachea condition sensors, the guide control device configured to process at least one of the detected existing trachea condition, introduced trachea condition, and signal of the trachea condition from the plurality of trachea condition sensors to determine an opening of the trachea and direct an insertion of the guide into the trachea in response to at least one of the detected trachea conditions.

15. The intubation device of claim 14, wherein the external trachea identifier source is configured to be mounted on a needle-like structure adapted to be embedded into the front neck.

16. The intubation device of claim 14, wherein the opening of the trachea and path of the guide into the trachea are determined based on an intensity or a level of at least one of the detected trachea conditions.

17. The intubation device of claim 14, further comprising a position sensor disposed on the guide tip, wherein the position sensor determines a position of the guide tip and provides feedback control to the guide control device.

18. The intubation device of claim 14, further comprising a video camera disposed on the guide tip to capture images of the opening of the trachea and an opening of an esophagus of the patient to monitor the insertion of the guide into the trachea.

19. The intubation device of claim 14, further comprising at least one conduit coupled to the guide wherein the conduit delivers medicine or performs one of a tissue biopsy, a laser treatment, a diagnostic procedure, and a therapeutic procedure.

20. A system of intubating a patient using an intubation device, the intubation device including a guide, a plurality of trachea condition sensors positioned on a tip of the guide, an external trachea identifier source that generates and transmits a signal detected by at least one of the plurality of trachea condition sensors on the tip of the guide, and a control device configured to move the guide, the system comprising:
 a user interface comprising a user input device and a display; and
 one or more actuators of the user input device to activate an operation of the intubation device, wherein the one or more actuators selectively activate the plurality of trachea condition sensors.

21. The system of claim 20, wherein the one or more actuators activate an automated or semi-automated intubation process.

22. The system of claim 20, wherein the one or more actuators are selectable to override an automated operation of the intubation.

23. The system of claim 20, further comprising processing real time information from a detected signal of the plurality of trachea condition sensors to determine an opening of a trachea and displaying the real time information on the user interface.

24. The system of claim 20, wherein the user interface includes an image display of an image captured by a video camera disposed on the guide tip.

* * * * *